(12) United States Patent
Adams

(10) Patent No.: US 6,629,630 B2
(45) Date of Patent: Oct. 7, 2003

(54) NON-CIRCULAR RESECTION DEVICE AND ENDOSCOPE

(75) Inventor: Ronald Adams, Holliston, MA (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/906,142

(22) Filed: Jul. 17, 2001

(65) Prior Publication Data
US 2003/0018236 A1 Jan. 23, 2003

Related U.S. Application Data

(60) Continuation-in-part of application No. 10/055,306, filed on Jan. 23, 2002, which is a continuation-in-part of application No. 09/813,944, filed on Mar. 22, 2001, now Pat. No. 6,343,731, which is a continuation of application No. 09/694,894, filed on Oct. 25, 2000, now Pat. No. 6,241,140, which is a continuation of application No. 09/316,674, filed on May 21, 1999, now Pat. No. 6,179,195, which is a division of application No. 09/100,393, filed on Jun. 19, 1998, now Pat. No. 6,126,058.

(51) Int. Cl.[7] .............................. A61B 17/04; A61B 1/00
(52) U.S. Cl. ........................ 227/180.1; 227/179.1; 600/127
(58) Field of Search .......................... 600/127, 128, 600/129, 105; 606/139; 227/176.1, 179.1, 180.1

(56) References Cited

U.S. PATENT DOCUMENTS

| | | |
|---|---|---|
| 1,185,292 A | 5/1916 | Astafiev |
| 2,905,178 A | 9/1959 | Hilzinger, III |
| 3,193,165 A | 7/1965 | Akhalaya et al. |
| 3,388,847 A | 6/1968 | Kasulin et al. |
| 3,452,615 A | 7/1969 | Gregory, Jr. |
| 3,552,626 A | 1/1971 | Astafiev |
| 3,638,652 A | 2/1972 | Kelley |
| 3,952,747 A | 4/1976 | Kimmell, Jr. |
| 4,047,654 A | 9/1977 | Alvarado |
| 4,108,211 A | 8/1978 | Tanaka |
| 4,155,452 A | 5/1979 | Wettermann et al. |
| 4,198,982 A | 4/1980 | Fortner et al. |
| 4,207,898 A | 6/1980 | Becht |
| 4,211,229 A | 7/1980 | Wurster |
| 4,261,346 A | 4/1981 | Wettermann |
| 4,285,376 A | 8/1981 | Ausnit |

(List continued on next page.)

FOREIGN PATENT DOCUMENTS

| | | |
|---|---|---|
| DE | 2 347 418 | 9/1973 |
| EP | 0 442 588 A2 | 8/1991 |
| GB | 2 016 991 A | 10/1979 |
| GB | 2 038 692 A | 7/1980 |
| WO | WO 93/15668 | 8/1993 |
| WO | WO 96/18344 | 6/1996 |

OTHER PUBLICATIONS

Waxman, Bruce et al., "Stapling in Colorectal Surgery," Surgery of the Colon, Rectum and Anus, W.B. Saunders Co., Philadelphia, 1995, pp. 778–811.

(List continued on next page.)

*Primary Examiner*—Linda C. M. Dvorak
*Assistant Examiner*—Kenneth Schopfer
(74) *Attorney, Agent, or Firm*—Fay Kaplun & Marcin LLP (57) ABSTRACT

A proximal housing for a full-thickness resection device (FTRD) is provided with a plurality of chambers through which fasteners are introduced into a portion of tissue to be resected. The proximal housing has a noncircular cut-out opposite the plurality of chambers to receive a noncircular endoscope. The proximal housing also is provided with a resection cavity into which the tissue to be resected is to be received. In addition, shaft openings are provided through which mounting shafts may be inserted. A noncircular endoscope is also disclosed for insertion into the cut-out whereby the endoscope has passages to house the functions of remote viewing, illumination, insufflation and irrigation.

11 Claims, 6 Drawing Sheets

U.S. PATENT DOCUMENTS

| | | |
|---|---|---|
| 4,304,236 A | 12/1981 | Conta et al. |
| 4,319,576 A | 3/1982 | Rothfuss |
| 4,351,466 A | 9/1982 | Noiles |
| 4,473,077 A | 9/1984 | Noiles et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,610,383 A | 9/1986 | Rothfuss et al. |
| 4,617,928 A | 10/1986 | Alfranca |
| 4,632,290 A | 12/1986 | Green et al. |
| 4,646,722 A | 3/1987 | Silverstein et al. |
| 4,667,673 A | 5/1987 | Li |
| 4,671,445 A | 6/1987 | Barker et al. |
| 4,716,900 A | 1/1988 | Ravo et al. |
| 4,741,326 A | 5/1988 | Sidall et al. |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,841,968 A | 6/1989 | Dunn et al. |
| 4,880,015 A | 11/1989 | Nierman |
| 4,886,049 A | 12/1989 | Darras |
| 4,893,622 A | 1/1990 | Green et al. |
| 4,907,591 A | 3/1990 | Vasconcellos et al. |
| 4,957,499 A | 9/1990 | Lipatov et al. |
| 5,005,749 A | 4/1991 | Aranyi |
| 5,009,643 A | 4/1991 | Reich et al. |
| 5,014,899 A | 5/1991 | Presty et al. |
| 5,015,249 A | 5/1991 | Nakao et al. |
| 5,025,778 A | 6/1991 | Silverstein et al. |
| 5,049,153 A | 9/1991 | Nakao et al. |
| 5,100,419 A | 3/1992 | Ehlers |
| 5,100,420 A | 3/1992 | Green et al. |
| 5,122,156 A | 6/1992 | Granger et al. |
| 5,139,513 A | 8/1992 | Segato |
| 5,156,609 A | 10/1992 | Nakao et al. |
| 5,158,222 A | 10/1992 | Green et al. |
| 5,171,222 A | 12/1992 | Euteneuer et al. |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,207,213 A * | 5/1993 | Auhll et al. ................ 600/104 |
| 5,219,111 A | 6/1993 | Bilotti et al. |
| 5,222,963 A | 6/1993 | Brinkerhoff et al. |
| 5,251,801 A | 10/1993 | Ruckdeschel et al. |
| 5,258,008 A | 11/1993 | Wilk |
| 5,259,366 A | 11/1993 | Reydel et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,314,435 A | 5/1994 | Green et al. |
| 5,314,436 A | 5/1994 | Wilk |
| 5,328,077 A | 7/1994 | Lou |
| 5,330,486 A | 7/1994 | Wilk |
| 5,333,773 A | 8/1994 | Main et al. |
| 5,344,059 A | 9/1994 | Green et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A * | 3/1995 | Kuramoto et al. ....... 227/179.1 |
| 5,395,034 A | 3/1995 | Allen et al. |
| 5,403,333 A | 4/1995 | Kaster et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,441,507 A | 8/1995 | Wilk |
| 5,443,198 A | 8/1995 | Viola et al. |
| 5,445,644 A | 8/1995 | Pietrafitta et al. |
| 5,447,514 A | 9/1995 | Gerry et al. |
| 5,454,825 A | 10/1995 | Van Leeuwen et al. |
| 5,465,895 A | 11/1995 | Knodel et al. |
| 5,474,223 A | 12/1995 | Viola et al. |
| 5,484,451 A | 1/1996 | Akopov et al. |
| 5,485,947 A | 1/1996 | Olson et al. |
| 5,485,952 A | 1/1996 | Fontayne |
| 5,522,534 A | 6/1996 | Viola et al. |
| 5,533,661 A | 7/1996 | Main et al. |
| 5,571,116 A | 11/1996 | Bolanos et al. |
| 5,609,285 A | 3/1997 | Grant et al. |
| 5,749,893 A | 5/1998 | Vidal et al. |
| 5,868,760 A | 2/1999 | McGuckin, Jr. |
| 6,119,913 A * | 9/2000 | Adams et al. ........... 227/176.1 |
| 6,126,058 A * | 10/2000 | Adams et al. ........... 227/179.1 |
| 6,179,195 B1 * | 1/2001 | Adams et al. ........... 227/179.1 |
| 6,241,140 B1 * | 6/2001 | Adams et al. ........... 227/176.1 |
| 6,302,311 B1 * | 10/2001 | Adams et al. ........... 227/176.1 |
| 6,343,731 B1 * | 2/2002 | Adams et al. ........... 224/176.1 |
| 6,383,198 B1 * | 5/2002 | Hamilton .................... 606/110 |

OTHER PUBLICATIONS

Swain, C. Paul et al., "An Endoscopic Stapling Device: the Development of a New Flexible Endoscopically Controlled Device for Placing Multiple Transmural Staples in Gastrointestinal Tissue," Gastrointestinal Endoscopy, American Society of Gastrointestinal Endoscopy, vol. 35, No. 4, 1989, pp. 338–339.

Swain C. Paul et al., "Knot Trying at Flexible Endoscopy," Gastrointestinal Endoscopy, American Society of Gastrointestinal Endoscopy, vol. 40, No. 6, 1994, pp. 722–729.

Swain C. Paul et al., "An Endoscopic Sewing Machine," Gastrointestinal Endoscopy, American Society of Gastrointestinal Endoscopy, vol. 32, No. 1, 1986, pp. 36–38.

Swain C. Paul et al., "An Endoscopically Deliverable Tissue–Transfixing Device for Securing Biosensors in the Gastrointestinal Tract," Gastrointestinal Endoscopy, American Society of Gastrointestinal Endoscopy, vol. 40, No. 6, 1994, pp. 730–734.

Escourrou, J. et al., "First Clinical Evaluation and Experimental Study of a New Mechanical Suture Device for Endoscopic Hemostasis," Gastrointestinal Endoscopy, American Society of Gastrointestinal Endoscopy, vol. 36, No. 5, 1990, pp. 494–497.

Pietrafitta, Joseph J. et al., "Experimental Transperitoneal Laparoscopic Pyloroplasty," Surgical Laparoscopy & Endoscopy, Raven Press, Ltd., New York, vol. 2, No. 2, 1992, pp. 104–110.

Hiller, Joe A., "Surgical Stapling Techniques," ETHICON a Johnson & Johnson Company, 1986.

* cited by examiner

NON-CIRCULAR RESECTION DEVICE AND ENDOSCOPE

PRIOR APPLICATIONS

This application is a continuation-in-part of U.S. application Ser. No. 10/055,306, filed Jan. 23, 2002, which is a continuation-in-part of U.S. application Ser. No. 09/813,944, filed Mar. 22, 2001 (issued as U.S. Pat. No. 6,343,731) which is a continuation of U.S. application Ser. No. 09/694,894 ("the '894 application"), filed Oct. 25, 2000 (issued as U.S. Pat. No. 6,241,140). The '894 application is a continuation of application Ser. No. 09/316,674, filed May 21, 1999 (issued as U.S. Pat. No. 6,179,195), which application is a division of application Ser. No. 09/100,393, filed Jun. 19, 1998 (issued as U.S. Pat. No. 6,126,058).

BACKGROUND OF THE INVENTION

1. Field of the Invention

The present invention relates generally to a full-thickness resection device (FTRD) for performing localized resections of lesions in tubular organs, particularly the colon. The present invention has particular application to transanal and transoral surgical procedures, although it is not limited thereto.

2. Description of the Related Art

A resection procedure involves excising a portion of an organ, approximating the surrounding tissue together to close up the hole created by the excision, and removing the excess tissue. Various conventional devices and procedures are available for resectioning lesions in tubular organs.

For example, several known resection devices and procedures require at least one incision in an area near the portion of the organ to be excised for access to the lesion or treatment site (because, for example, the resectioning device may lack steering and/or viewing capabilities). Thus, the incision is required to allow the physician to access the organ section to be excised and guide the device to that section. Alternatively, when the organ section to be excised is beyond the reach of the surgical device, or the surgical device is not flexible enough to wind through the organ to the site to be excised, an incision will be required to position the device for the procedure. Of course, these incisions are painful and may involve a partial or entire loss of mobility while recuperating from the incision, in addition to recovering from the tubular resectioning procedure itself. In addition, the time required to recover from such a procedure is often longer than for procedures which do not require incisions.

One type of conventional resection procedure utilizes a circular stapling instrument in which a tubular section of a tubular organ is excised, resulting in the tubular organ being separated into a first segment and a second segment. The end sections of the first and second segments are then individually tied in a purse-string fashion, approximated, stapled, and the "purse-stringed" end sections are then cut off. In this full circle resectioning procedure, at least one separate invasive incision must be made near the section to be excised in order to cut and individually tie the separate end sections of the organ. Also, a separate incision is necessary to place one part of the resectioning device in the first segment and a corresponding second part of the device in the second segment so that the device can then bring the first and second segments together to re-attach the organ sections back together. A first of these separate parts may generally include a staple firing mechanism while the second part includes an anvil for forming the staples. Thus, this type of resectioning procedure involves the drawbacks mentioned above in regard to procedures requiring invasive incisions. In addition, the separation of the organ into two segments creates the risk of spillage of non-sterile bowel contents into the sterile body cavity, which can cause severe infection and possibly death.

An alternative resectioning device includes a stapling and cutting assembly on a shaft which can be bent or formed into a desired shape and then inserted into a patient's body cavity. Once the shaft has been bent into the desired shape, the rigidity of the shaft ensures that that shape is maintained throughout the operation. This arrangement limits the effective operating range of the device as the bending of the shaft into the desired shape before insertion and the rigidity of the shaft once bent require the physician to ascertain the location of the organ section to be removed before insertion, and deform the shaft accordingly. Furthermore, the rigidity of the shaft makes it difficult to reach remote areas in the organ—particularly those areas which must be reached by a winding and/or circuitous route (e.g., sigmoid colon). Thus, an incision may be required near the organ section to be excised in order to position the device at the organ section to be excised.

Currently such FTRD's incorporate standard endoscopes available from various manufacturers. These standard endoscopes are circular in shape, and while a circular shape is desirable in many conventional applications where the endoscope is used independently, with FTRD's, a circular endoscope, for example, takes up significant space in the body lumen. This can result in a sample having a smaller size than desired. A circular endoscope also may not have sufficient flexibility to bend to a desired location.

SUMMARY OF THE INVENTION

In accordance with the invention, a proximal housing for a full-thickness resection device (FTRD) is provided with a plurality of chambers through which fasteners are introduced into a portion of tissue to be resected. The proximal housing has a noncircular cut-out opposite the plurality of chambers to receive a noncircular endoscope. The proximal housing also is provided with a resection cavity into which the tissue to be resected is to be received. In addition, shaft openings are provided through which mounting shafts may be inserted.

According to another aspect of the invention, the plurality of chambers is configured so as to provide a substantially elliptical fastener pattern.

According to yet another aspect of the invention, the fasteners used are staples.

According to another aspect of the invention, a noncircular endoscope is also disclosed that is substantially the same shape as the cut-out for insertion into the cut-out whereby the endoscope has passages to house the functions of remote viewing, lighting, insufflation and irrigation.

According to another aspect of the invention, the noncircular endoscope is elliptical in shape.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. Both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate one embodiment of the invention and together with the description, serve to explain the principles of the invention.

DESCRIPTION OF THE EMBODIMENTS

The present invention is directed to a non-circular endoscope and corresponding FTRD. These non-circular devices have numerous advantages over existing circular devices. For example, the non-circular shape allows the device to take up less space within the body lumen into which it is being inserted. The non-circular endoscope also provides a more efficient means of packaging the combination of the device and endoscope. The more efficient utilization of space enables a device that can capture larger specimen sizes than an equivalent circular endoscope would permit. In addition, a non-circular endoscope for use with an FTRD may be more flexible and therefore more easily bend forwards a desired location, due, for example, to the smaller cross-sectional area of the endoscope. In preferred embodiments, the endoscope is shaped for particular use in combination with devices that perform a full thickness resection or similar procedure. In addition, the shape of a staple cartridge and anvil of the devices has a more elliptical, non-circular staple pattern that also provides further advantages.

Reference will now be made in detail to the present embodiments of the invention, examples of which is illustrated in the accompanying drawings. Wherever possible, the same reference numbers will be used throughout the drawings to refer to the same or like parts.

Figure 1:
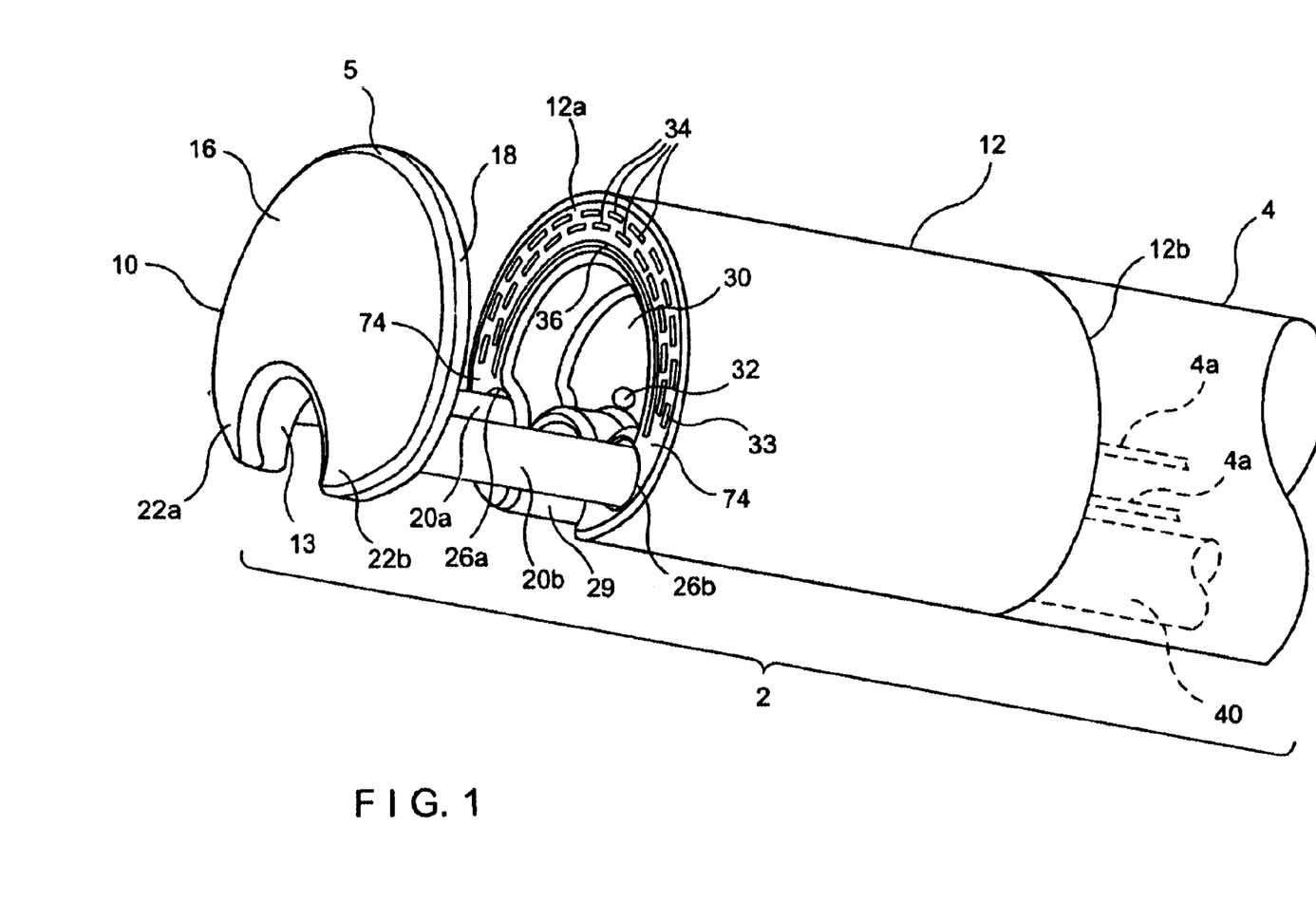
FIG. 1 is a perspective view showing a full-thickness resection device according to an embodiment of the present invention.
Figure 2:
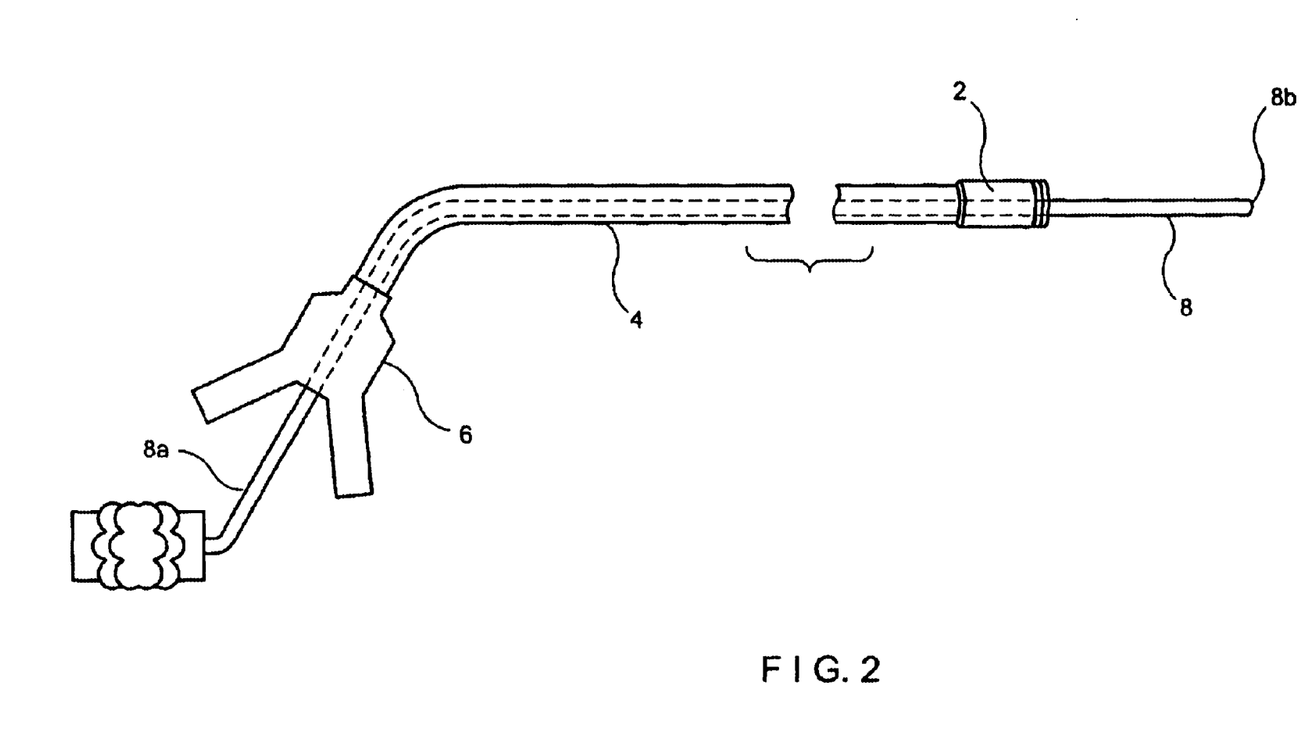
FIG. 2 is a perspective view showing the device of FIG. 1 mounted on an it endoscope according to an embodiment of the present invention.

As shown in FIGS. 1 and 2, an FTRD comprises a working head assembly 2 which may be connected to a distal end 4a of a sheath 4. The proximal end of the sheath 4 may be connected to a control handle 6. In operation, the entire apparatus is mounted onto an endoscope 8, having a proximal end 8a and a distal end 8b, by passing the endoscope 8 through the control handle 6, the sheath 4, and the working head assembly 2, as shown in FIG. 2. The endoscope 8 is then inserted into a body orifice to locate a lesion in the tubular organ under visual observation (usually while insufflating the organ). Once the lesion has been located, the, working head assembly 2 and the sheath 4 are slidably advanced along the endoscope 8 into the tubular organ until the working head assembly 2 is in a desired position adjacent to the lesion. Those skilled in the art will understand that in an alternative embodiment, the working head assembly 2 may also be detachably coupled to a distal end of the endoscope 8, and the entire arrangement may then be inserted into the body orifice under visual observation.

As shown in FIG. 1, the working head assembly 2 comprises an anvil member 10 coupled to a distal end 12a of a proximal housing 12. The anvil member 10 has a substantially crescent-shaped cross-section (i.e., the outer edge 18 of the anvil member 10 substantially forms a portion of a first ellipse with a second smaller elliptical cut-out 13 formed within the first ellipse) with a distal face 16 and a larger proximal face opposite the distal face. The cut-out 13 of the anvil member 10 is included to allow the endoscope 8 to be slid through the entire working head assembly 2 so that the endoscope 8 may be advanced into the body passage allowing the working head assembly 2 to later be advanced into the body to the lesion. In addition, the cut-out 13 also provides forward vision via the endoscope 8. Thus, any shape of the cut-out 13 may be selected which is large enough to accommodate the endoscope 8, with a larger cut-out providing a larger field of vision. An outer surface 18 of the anvil member 10 extends substantially parallel to a central axis of the working head assembly 2 while the proximal and distal faces of the anvil member 10 extend in planes substantially perpendicular to the central axis. The outer surface 18 is joined to the distal face 16 by a tapered portion 5.

Figure 3:
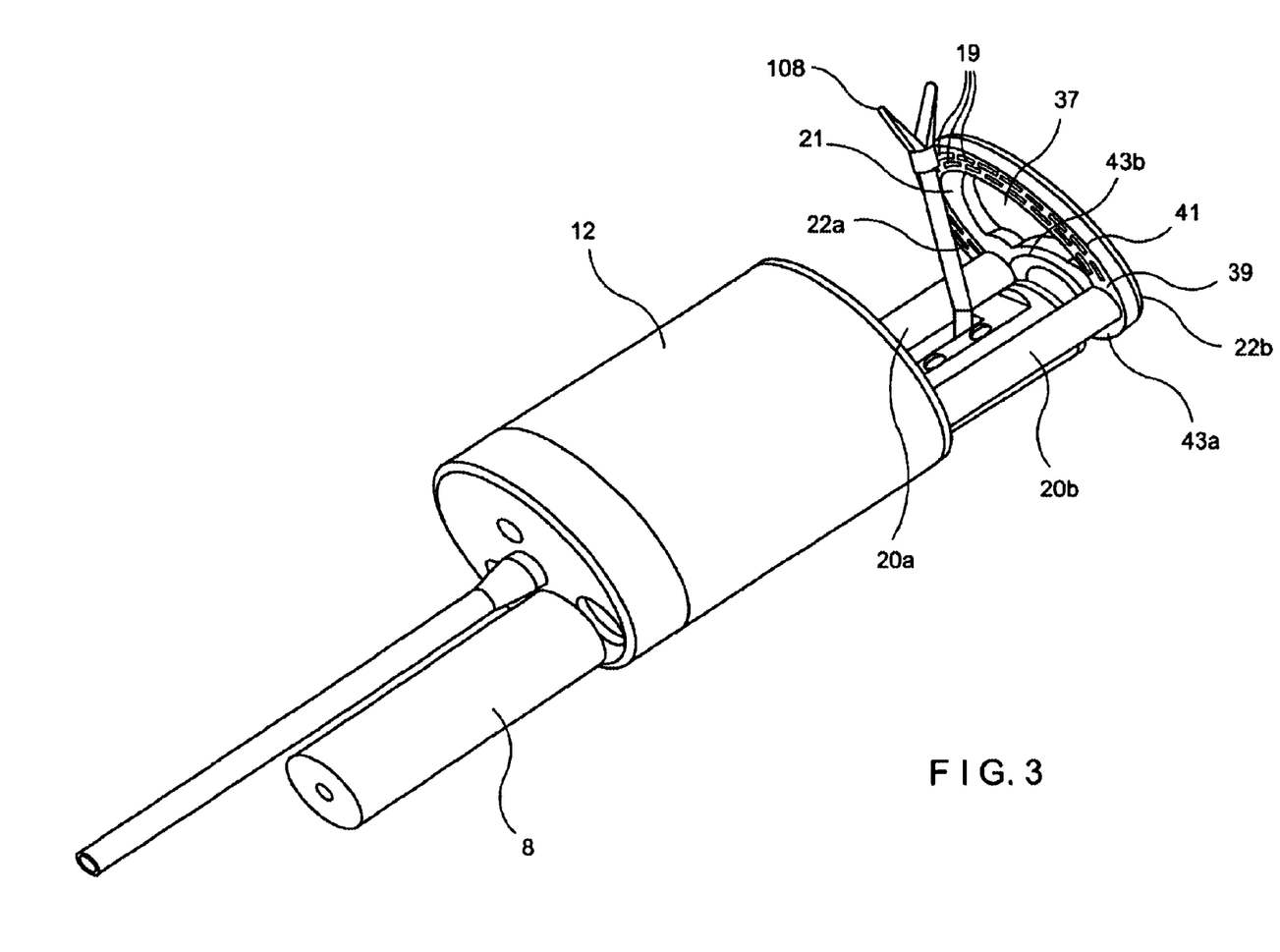
FIG. 3 is a perspective view showing the device of FIG. 1 with a grasper mechanism extending therefrom.

As shown in FIG. 3, the proximal face of the anvil member 10 includes a first cavity 37 and a rim 41 encircling the first cavity 37. A plurality of staple-forming grooves 19 are arranged in two offset rows on the rim 41 of the anvil member 10 and an elliptical guiding slit 21 extends radially within the rows of grooves 19. The rim 41 protrudes from the remainder of the proximal face so that a shallow cavity is formed on the proximal face.

The anvil member 10 is coupled to the proximal housing 12 by means of two mounting shafts 20a and 20b, which may be substantially cylindrical. Each mounting shaft 20a, 20b is coupled to the proximal face 14 of the anvil member 10 on a respective one of two horns 22a, 22b formed by the crescent-shaped anvil member 10. Although the anvil member 10 is shown fixedly coupled to the mounting shafts 20a, 20b, those skilled in the art will understand that the anvil member 10 may also be pivotally coupled to the mounting shafts 20a, 20b in order to provide a greater field of vision through the endoscope 8, as shown in FIG. 3. In this pivoted-type arrangement, the anvil member 10 is angled in a first configuration so that the horns 22a, 22b are closer to the distal end 12a of the proximal housing than the rest of the anvil member 10. Then, as the anvil member 10 is drawn towards the distal end 12a of the proximal housing 12, the anvil member 10 would be pressed against the distal end 12a beginning with the horns 22a, 22b, which would cause the anvil member 10 to pivot until the proximal face 14 of the anvil member 10 is parallel to the distal end 12a.

As shown in FIG. 1, the mounting shafts 20a, 20b are slidably received in mounting holes 26a, 26b, which have a size and shape substantially corresponding to the size and shape of the mounting shafts 20a, 20b and which run axially through the proximal housing 12. The mounting shafts 20a, 20b are preferably movable axially proximally and distally within the mounting holes 26a, 26b between a proximal most position in which a tissue gripping gap of a first predetermined width is formed between the rim 41 and the distal end 12a of the proximal housing 12, and a distal most position in which a tissue receiving gap of a larger second predetermined width is formed between the rim 41 and the distal end 12a of the proximal housing 12. The second predetermined width should preferably be more than twice the thickness of a wall of the organ being resectioned so that a section of the tubular organ may be pulled into a resectioning position between the anvil member 10 and the proximal housing 12.

Figure 4:
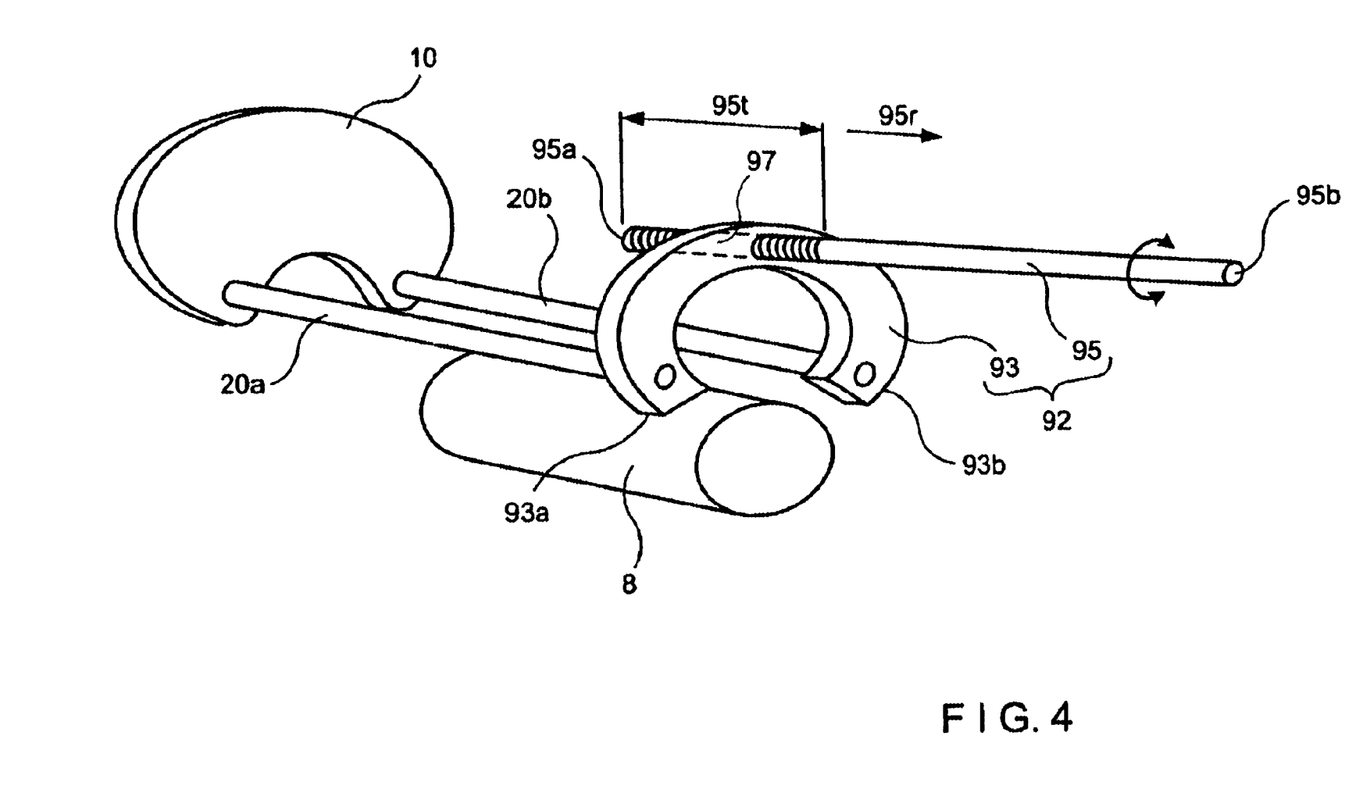
FIG. 4 is a perspective view showing a drive mechanism of FIG. 1.
Figure 5:
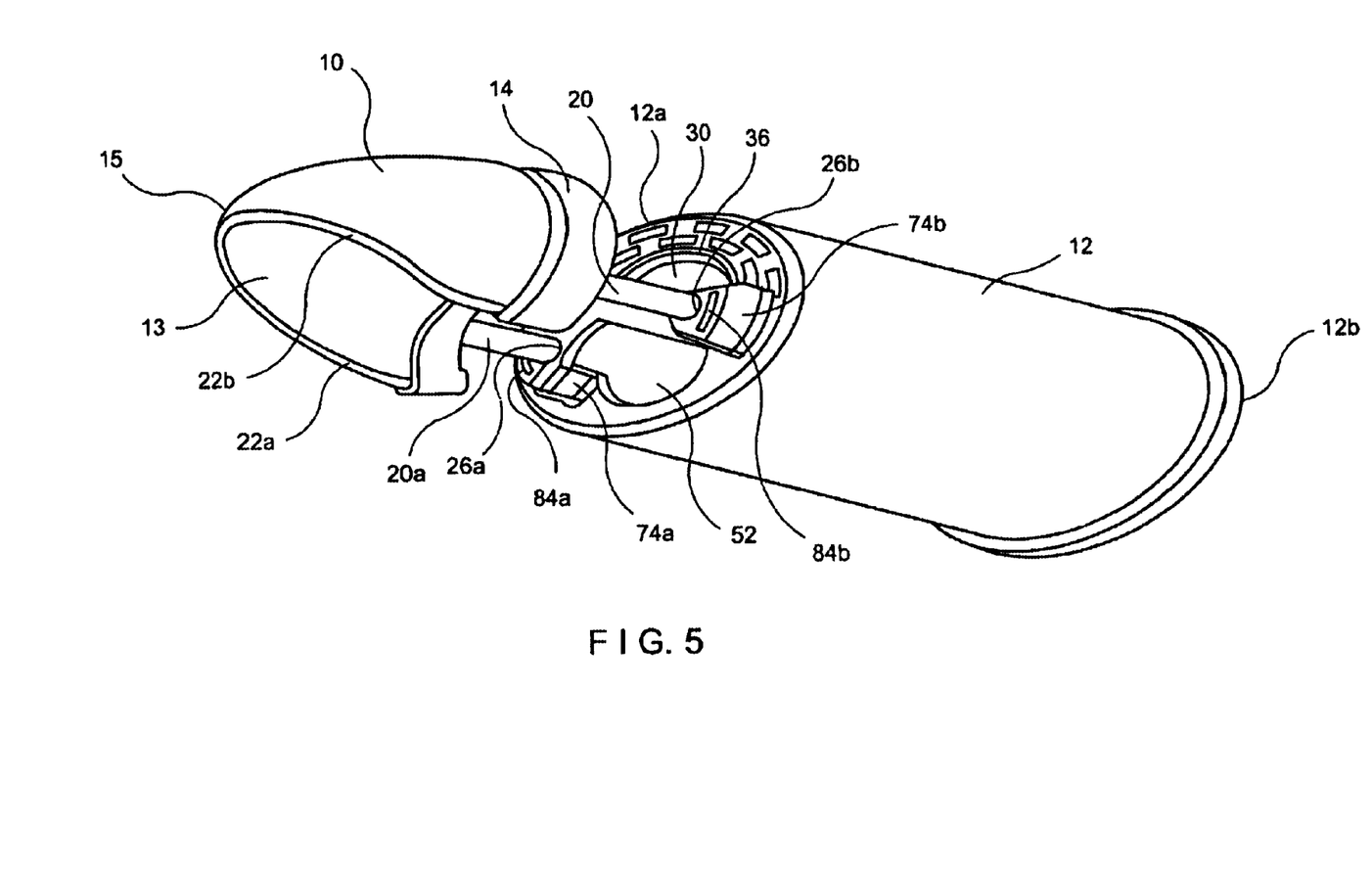
FIG. 5 is a perspective view showing the device of FIG. 1 with a tapered end for ease of insertion.

As shown in FIG. 4, the proximal end of at least one of the mounting shafts 20a and 20b is coupled to a drive mechanism 92 provided within the proximal housing 12. The drive mechanism 92 is composed of a yoke 93 and a drive shaft 95. The yoke 93 is slidably received within the proximal housing 12 for longitudinal movement along the axis of the proximal housing 12 so that, when the anvil member 10 is in the proximal most position, the yoke 93 is in a corresponding proximal most position and, when the anvil member is in the distal most position, the yoke 93 is in a corresponding distal most position.

The yoke 93 may be substantially elliptical with a substantially rectangular cross-section. Although the ellipse formed by the yoke 93 in FIG. 4 forms substantially a quarter arc of a ellipse, the yoke 93 may form a larger ellipse based upon the interior accommodations of the proximal housing 12 and the position of the mounting shafts 20a, 20b. The mounting shaft 20a may preferably be coupled to the yoke 93 at a first end 93a of the yoke 93, and the mounting shaft 20b may be coupled at a second end 93b of the yoke 93. A shaft hole 97, having a diameter substantially corresponding to a diameter of a complementarily threaded distal end 95a of the drive shaft 95, extends through the yoke 93 at a point substantially midway between the first end 93a and second end 93b. Thus, when the drive shaft 95 is rotated, the threaded distal end 95a engages the shaft hole 97 to move the yoke 93 proximally or distally (in dependence upon the direction of rotation of the drive shaft 95).

The distal end 95a of the drive shaft 95 should preferably be threaded over a first section 95t substantially corresponding in length to at least the distance between the proximal and distal most yoke positions, while a remainder portion 95r may have no threads thereon. The drive shaft 95 may have an increased cross-section in the areas immediately adjacent to the threaded first section 95t (proximally and/or distally of section 95t), thereby limiting the movement of the yoke 93 to the first section 95t. Those skilled in the art will understand that the drive shaft 95 is rotatably mounted within the proximal housing 12 so that it may only rotated and may not move relative to the proximal housing 12. The drive shaft 95 extends to a proximal end 95b which is coupled to a drive cable 90 which extends to the control handle 6 through the sheath 4. The drive cable 90 may run axially along the peripheral interior of the sheath 4. Those skilled in the art will understand that the sheath 4 is torsionally stiff to resist the torque forces from the drive cables rotating therein. However, the sheath 4 is longitudinally flexible to so that it may be slidably advanced along the endoscope 8, while minimizing interference with the operation of the endoscope 8 and trauma to surrounding tissue. The sheath 4 is constructed similar to other known endoscope insertion tubes, which are flexible yet allow the transfer of forces to swivel the distal end of the endoscope 8 in multiple directions and the torqueable rotation of the endoscope.

In operation, the user advances the endoscope 8, with the working head assembly 2 received therearound, to a portion of tissue to be resectioned until the working head assembly 2 is in a desired position adjacent to the tissue to be resectioned. The user may then apply a force to the control handle 6 to rotate the drive cable 100, as seen in FIG. 4, which in turn rotates the drive shaft 95 to advance the yoke 93 and the anvil member 10 distally away from the distal end 12a of the proximal housing 12. As shown in FIG. 3 when the anvil member 10 has reached the distal most position, a known grasping device 98 is advanced through the sheath 4 and through the working head assembly 2 to enter the gap between the anvil member 10 and the distal end 12a via one of the grasper holes 32 and 33. Although the device in FIG. 3 is shown using a duodenoscope as the endoscope 8, those skilled in the art will understand that other types of endoscopes may also be used, such as, for example, gastroscope, colonoscope, etc.

As shown in FIG. 1, at least the distal end 12a of the proximal housing 12 has a cross-section corresponding in size and shape to the proximal face 14 of the anvil member 10, including a cut-out 29 substantially corresponding in size and shape to the cutout 13 of anvil member 10. The cut-out 29 is provided to receive the endoscope 8 therein and allow the proximal housing 12 to be slidably advanced along the endoscope 8. Of course, those skilled in the art will understand that the shape of the outer surface of the working head assembly 2 may be selected in order to accommodate various desired resectioning shapes, and the shape of the anvil member 10 may preferably be selected to form a continuous surface when positioned adjacent to the proximal housing 12 to facilitate advancing the working head assembly to into and removing it from, body passages. It is preferable that the working head assembly have a maximum diameter at any point between 15 mm and 40 mm.

A tissue receiving cavity 30 is formed substantially centrally in the distal end 12a of the proximal housing 12 to facilitate the drawing of sections of tubular organs into the gap between the anvil member 10 and the distal end 12a. Those skilled in the art will understand that the depth of the cavity 30 may vary depending on the amount of tissue to be pulled into the cavity 30 and the size of the proximal housing 12. Two grasper holes 32 and 33 extend axially, preferably slightly off-center from the longitudinal axis of the proximal housing 12. The grasper holes 32 and 33 may each receive a grasping device 108 advanced from the control handle 6, through the sheath 4, and through a respective one of the grasper holes 32 and 33.

In operation, either one or two grasping devices 98 may then be used to pull a section of the tubular organ between the anvil member 10 and the distal end 12a of the proximal housing 12 and into the cavity 30. A third grasping device 98 may also be inserted through the working channel of the endoscope 8 to provide another means of positioning the organ section between the anvil member 10 and the proximal housing 12. Of course, those skilled in the art will understand that any desired instrument may be advanced to the gap between the anvil member 10 and the distal end 12a through any of the grasper holes 32, 33 and the working channel of the endoscope 8.

A plurality of staple slits 34 are preferably disposed in two offset substantially elliptical rows extending along the periphery of the distal end 12a of the proximal housing 12. The staple slits 34 extend from an area adjacent to the mounting shaft 26a to an area adjacent to the other mounting shaft 26b. The plurality of staple slits 34 may be arranged so that when the anvil member 10 is in the proximal most position, each of the staple slits 34 is aligned with a corresponding one of the staple-forming grooves 19.

When the device is configured for operation, a plurality of staples is received within the working head assembly 2 with each of the staples being aligned with a respective one of the staple slits 34. The staples are then sequentially fired from the respective staple slits 34 by an actuating mechanism (not shown) disposed in the proximal housing 12.

A substantially elliptical blade slit 36 extends substantially radially within the staple slits 34 so that, when the anvil is in the proximal most position, the blade slit 36 is aligned with the guiding slit 21 on the anvil member. As shown more clearly in FIG. 4, extensions 84a and 84b of the blade slit 36 extend into blade housings 74a and 74b, respectively, which project distally from the distal end 12a of proximal housing 12. The blade housings 74a and 74b are preferably situated so that when the anvil member 10 is in its proximal most position, the blade housings 74a and 74b contact portions 43a and 43b of the rim 41 of the anvil member 10. The extension of the blade housings 74a and 74b from the proximal housing 12 is preferably selected so that when the blade housing devices 74a and 74b engage the remainder portions 43a and 43b of the rim 41 (thereby stopping a proximal movement of the anvil member 10 and defining the proximal most position thereof), a gap is formed between the anvil member 10 and the distal end 12a of a length sufficient to allow the anvil member 10 to securely hold a portion of the organ against the proximal housing 12 without crushing and damaging the portion of the organ.

When positioned at one end of the blade slit 36 (i.e., in one of the extensions 84a and 84b), a cutting blade (not shown) is preferably completely enclosed within the respective one of the blade housing devices 74a and 74b and the guiding slit 21, so that the cutting blade does not cut any tissue until the physician intentionally operates the blade. When the physician operates the blade, the blade is driven from its initial position received within one of the extensions 84a and 84b around the blade slit 36 with its cutting edge facing a direction of movement, until the blade is received into the other one of the extensions 84a and 84b. Thus, after a cutting operation has been performed, the blade is once again prevented from inadvertently injuring the patient.

As can be seen in the prior art devices utilizing a circular endoscope, the endoscope occupies significant space within the FTRD and also encroaches upon the resection cavity. With the prior art devices, in order to provide a cavity of the size necessary to perform the desired surgical procedure, the overall size of the FTRD must be made larger.

Figure 6:
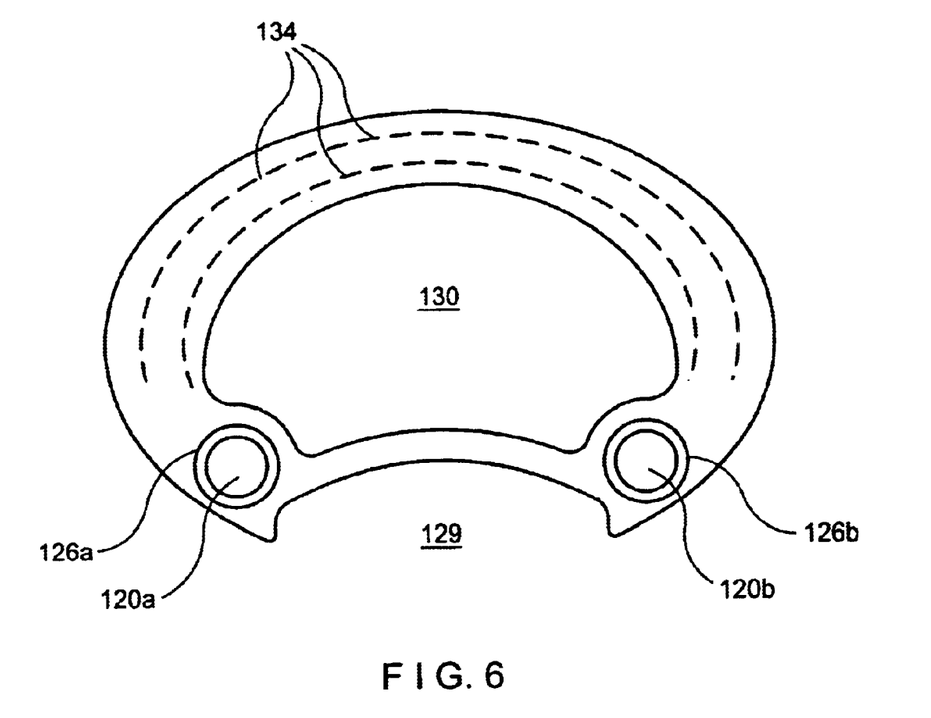
FIG. 6 is a cross-sectional view of a proximal housing of a full-thickness resection device, according to an embodiment of the present invention.

FIG. 6 shows a cross section of a proximal housing 112 of an FTRD, and is configured to receive a non-circular endoscope within cut-out 129. Proximal housing 112 also contains mounting holes 126a and 126b as well as mounting shafts.

As can be seen, cut-out 129 does not extend into cavity 130 as much as in the prior art devices, thus allowing the overall size of proximal housing 112 to be reduced. In addition, the elliptical shape of the head provides a more desirable elliptically shaped staple pattern for the staples ejected from chambers 134 than the partial circular pattern of the prior art devices.

Figure 7:
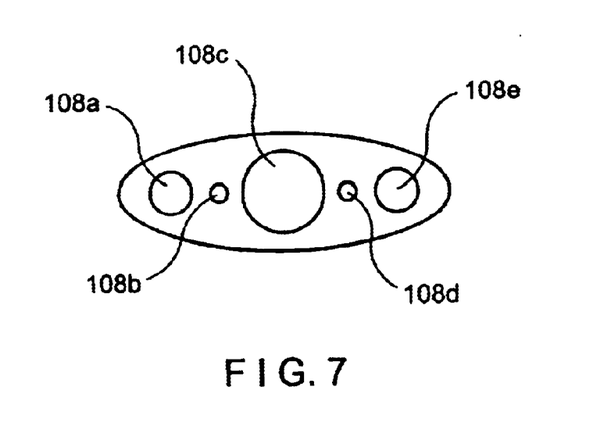
FIG. 7 is a cross-sectional view showing an endoscope to be used with the device of FIG. 6.

Endoscope 108, as seen in FIG. 7, is an endoscope of the present embodiment to fit within cut-out 129. Rather than using a standard circular endoscope of the prior art devices that may provide more chambers than what is necessary for a full-thickness resection procedure, the current invention relates to an endoscope that provides only what is needed for the desired procedure. Endoscope 108 can be provided with as few as four chambers to house the functions used to perform this procedure: remote viewing, lighting, insufflation and irrigation.

According to the present embodiment, endoscope 108 has an elliptical shape to fit within cut-out 129 of proximal housing 112. Those skilled in the art would understand that other noncircular shaped endoscopes could be utilized that provide the same low-profile shape that the elliptical shape provides. Provided within endoscope 108 are five chambers 108a–108e. Chamber 108c preferably houses the optics portion of the endoscope. Chambers 108b and 108d contain light sources to illuminate the area in which the procedure is to be performed. Chambers 108a and 108e may provide the insufflation and irrigation functions of the endoscope, respectively, although one of ordinary skill in the art could comprehend that these functions may be reversed. In operation an FTRD utilizing proximal housing 112 will function in the same manner as the prior art FTRD's.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A proximal housing for a full-thickness resection device comprising:
   a plurality of chambers through which fasteners are introduced into a portion of tissue to be resected;
   a noncircular cut-out formed in the proximal housing opposite the plurality of chambers to receive an endoscope;
   a resection cavity into which the portion of tissue is to be received;
   at least one shaft opening through which a mounting shaft may be inserted; and
   a noncircular endoscope of substantially the same shape as the noncircular cut-out inserted into said noncircular cut-out.

2. The proximal housing of claim 1, wherein the plurality of chambers are configured so as to produce an essentially elliptical fastener pattern.

3. The proximal housing of claim 1, wherein the noncircular endoscope contains an optical source, at least one light source, an insufflation passage and an irrigation passage.

4. The proximal housing of claim 1, wherein the fasteners are staples.

5. The proximal housing of claim 1, wherein at least one shaft opening includes two shaft openings.

6. The proximal housing of claim 1, wherein the noncircular endoscope is elliptical in shape.

7. A proximal housing for a full-thickness resection device comprising:
   a plurality of chambers through which fasteners are introduced into a portion of tissue to be resected;
   a noncircular cut-out formed in the proximal housing opposite the plurality of chambers to receive an endoscope of noncircular shape;
   a resection cavity into which the portion of tissue is to be received; and
   at least one shaft opening through which a mounting shaft may be inserted.

8. The proximal housing of claim 7, wherein the plurality of chambers are configured so as to produce an essentially elliptical fastener pattern.

9. The proximal housing of claim 7, wherein the fasteners are staples.

10. The proximal housing of claim 7, wherein at least one shaft opening includes two shaft openings.

11. The proximal housing of claim 7, wherein the noncircular cut-out is elliptical.

* * * * *